United States Patent [19]

Manabe

[11] Patent Number: 5,054,049
[45] Date of Patent: Oct. 1, 1991

[54] PATIENT SUPPORT MEANS FOR X-RAY ABSORPTION COMPENSATION IN COMPUTER TOMOGRAPHY SYSTEM

[75] Inventor: Yoshinori Manabe, Ootawara, Japan

[73] Assignee: Kabushiki Kaisha Toshiba, Kawasaki, Japan

[21] Appl. No.: 496,581

[22] Filed: Mar. 21, 1990

[30] Foreign Application Priority Data

Mar. 22, 1989 [JP] Japan .................................. 1-67604

[51] Int. Cl.$^5$ .......................... H05G 1/00; A61B 6/04
[52] U.S. Cl. .................................... 378/208; 378/209; 378/20
[58] Field of Search ............... 378/113, 195, 4, 20, 378/208, 209, 161

[56] References Cited

U.S. PATENT DOCUMENTS

| | | |
|---|---|---|
| 3,449,570 | 6/1969 | Kok . |
| 3,947,686 | 3/1976 | Copper et al. ............... 378/209 |
| 4,146,793 | 3/1979 | Bergstrom et al. ........... 378/161 |
| 4,211,926 | 7/1980 | Nakaya et al. ............... 378/20 |
| 4,262,204 | 4/1981 | Mirabella .................... 378/20 |
| 4,278,888 | 7/1981 | Wagner ....................... 378/20 |
| 4,303,829 | 12/1981 | Wagner ....................... 378/20 |
| 4,558,458 | 12/1985 | Katsumata et al. ........... 378/20 |
| 4,606,062 | 8/1986 | Saito .......................... 378/113 |
| 4,651,355 | 3/1987 | Kalender et al. ............. 378/20 |
| 4,905,267 | 2/1990 | Miller et al. ................. 378/208 |
| 4,926,457 | 5/1990 | Poehner et al. .............. 378/209 |

FOREIGN PATENT DOCUMENTS 1039192 9/1958 Fed. Rep. of Germany .
2110690 6/1972 France .

Primary Examiner—Edward P. Westin
Assistant Examiner—Kim-Kwok Chu
Attorney, Agent, or Firm—Cushman, Darby & Cushman

[57] ABSTRACT

The x-ray absorption factor of each end section of a top table is lower than that of a middle section thereof. If the end section of the top table protrudes from an effective field of scan so that fan beams are transmitted through the protruded portion, the beams can hardly be absorbed by the protruded portion. Accordingly, projection data obtained are hardly subject to any significant differences which depend on the transmission of the fan beams. Even though an image is reconstructed in accordance with the obtained projection data, therefore, it can be restrained from suffering shading. Thus, a high-quality image can be obtained.

5 Claims, 4 Drawing Sheets

PATIENT SUPPORT MEANS FOR X-RAY ABSORPTION COMPENSATION IN COMPUTER TOMOGRAPHY SYSTEM

BACKGROUND OF THE INVENTION

The present invention relates to an x-ray computed tomography (hereinafter referred to as CT) scanner apparatus, and more particularly, to an arrangement of a member adapted to hold an examined object in position.

2. Description of the Related Art

In an x-ray CT apparatus, e.g., a third-generation x-ray CT apparatus, x-ray fan beams are emitted from an x-ray source while the x-ray source and a multi-channel x-ray detector are being revolved around an examined body, and the beams are detected by means of the detector. The detector delivers a signal proportional to the detected amount of x-rays to a signal processing circuit, whereupon the signal is processed by the processing circuit. Thereafter, projection data are supplied from the signal processing circuit to an image reproducing circuit. Based on these projection data, a slice image of the examined body is reconstructed and displayed on a display unit.

In order to obtain an image of a slice plane of the examined object, data on projection from all directions (360°) for all the area of the slice plane must be prepared. To attain this, the x-ray source and the detector are revolved around a revolution center so that the x-ray fan beams are revolved around the revolution center while the slice plane of the object is being scanned therewith. In this manner, a circle obtained by superposing the revolved fan beams is defined as an effective field of scan.

Thus, if a top plate of a bed unit as well as the examined object, is situated within the effective field, perfect tomography can be effected. However, part of the top plate sometimes may protrude from the effective field. Such a case involves the following problems. Although the fan beams may be transmitted through the protruded portion if the x-ray source is situated in one position, they may not if the x-ray source is situated in another position. If the beams are transmitted through the protruded portion, therefore, the projection data obtained include data on x-rays absorbed by the protruded portion. If the beams are not transmitted through the protruded portion, however, the obtained data do not include the data on the x-rays absorbed by the protruded portion. Accordingly, there are significant differences between the projection data, depending on the transmission of the fan beams. Thus, the resulting reconstructed image sometimes may be subject to shading.

In order to improve the resolution of the image, moreover, the x-ray source and the detector may be shifted around the revolution center to make the effective field of scan relatively small. In this case, part of the top plate is particularly liable to protrude thus entailing the problem of shading.

SUMMARY OF THE INVENTION

The present invention has been contrived in consideration of these circumstances, and its object is to provide an x-ray CT scanner apparatus, capable of producing a shading-free image of high quality, without entailing any significant differences between projection data obtained, even though part of a member for supporting an examined object protrudes from an effective field of scan.

According to the present invention, there is provided an x-ray computed tomography scanner apparatus which comprises: means for radiating an x-ray fan beam to an examined object, so that the object is scanned with the fan beam along a slice plane; means for detecting the scanned fan beam to prepare x-ray transmission data, so that an image of the slice plane of the object can be reconstructed in accordance with the data; and means for supporting the object, the supporting means including a middle section and an end section located in the middle and at the end thereof, respectively, when the supporting means is cut along the slice plane, so that the x-ray absorption factor of the end section is lower than that of the middle section.

The end section of the object supporting means, e.g., a table, has a lower x-ray absorption factor than that of the middle section thereof. If the end section of the supporting means for the examined object protrudes from an effective field of scan so that the fan beams are transmitted through the protruded portion, the beams can hardly be absorbed by the protruded portion. Accordingly, projection data obtained are hardly subject to any significant differences which depend on the transmission of the fan beams. Even though an image is reconstructed in accordance with the obtained projection data, therefore, it can be restrained from suffering shading. Thus, a high-quality image can be obtained.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate a presently preferred embodiment of the invention, and together with the general description given above and the detailed description of the preferred embodiment given below, serve to explain the principles of the invention.

DETAILED DESCRIPTION OF THE PREFERRED EMBODIMENTS

Figure 1:
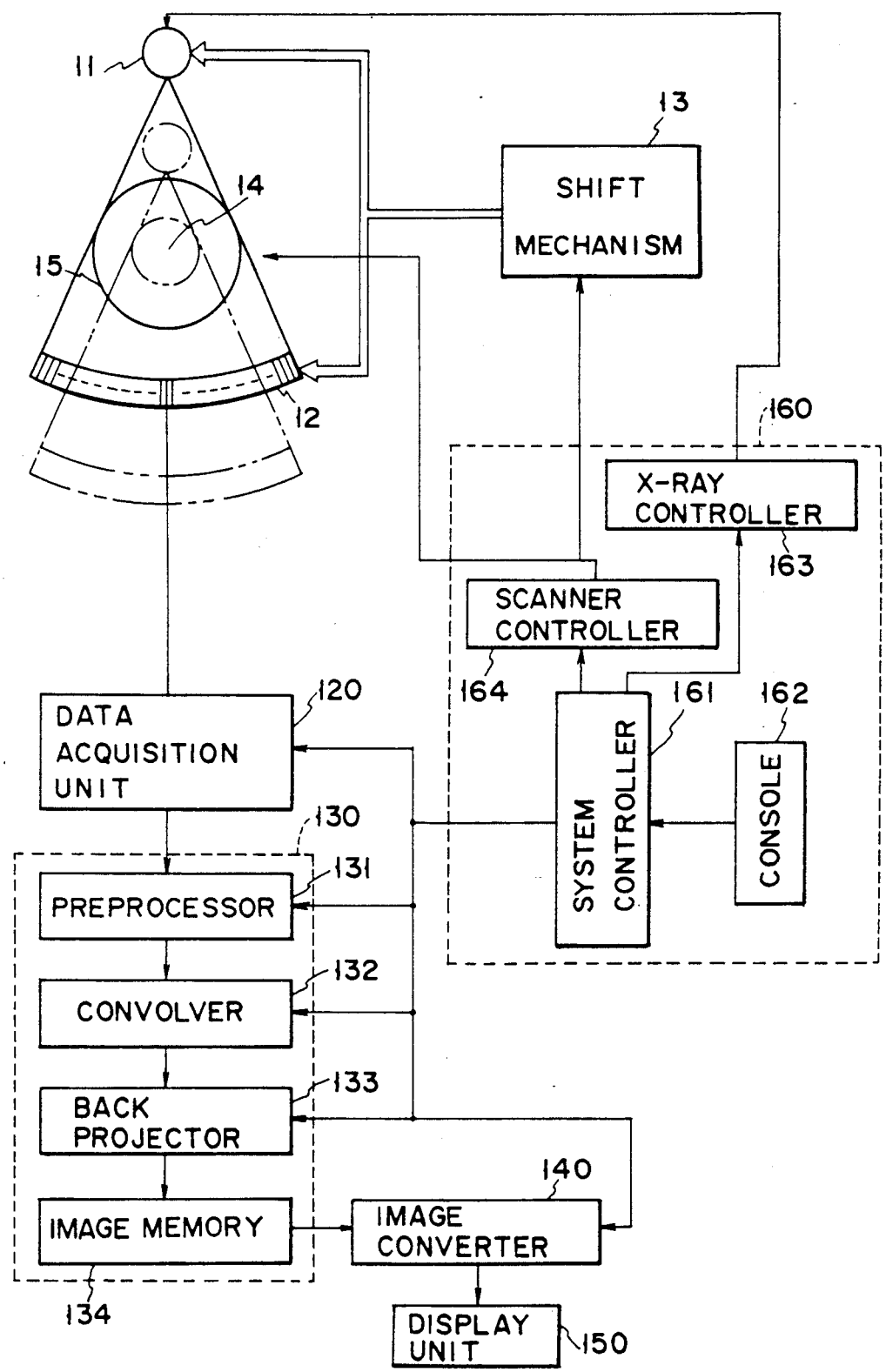
FIG. 1 is a schematic view showing an x-ray CT apparatus according to an embodiment of the present invention.

FIG. 1 shows an x-ray CT apparatus according to an embodiment of the present invention. A gantry (not shown) is provided with x-ray tube 11 for emitting x-ray fan beams, and multichannel x-ray detector 12 opposed to the x-ray tube. While x-ray tube 11 and detector 12 are being revolved around revolution center 14, x-ray fan beams are emitted from tube 11, and are detected by detector 12. Thereupon, projection data are obtained, and a slice image of an examined body is reconstructed in accordance with the data, as mentioned later. A circle obtained by superposing the revolved fan beams is defined as effective field 15 of scan.

In this embodiment, as shown by two dot line in FIG. 1, x-ray tube 11 and detector 12 can be shifted relatively to revolution center 14 by means of shift mechanism 13. Thus, effective field 15 can be enlarged or reduced. If the effective field is made smaller, then the number of x-ray beams per unit length increases in proportion, so that the resolution of the image is improved.

Figure 2:
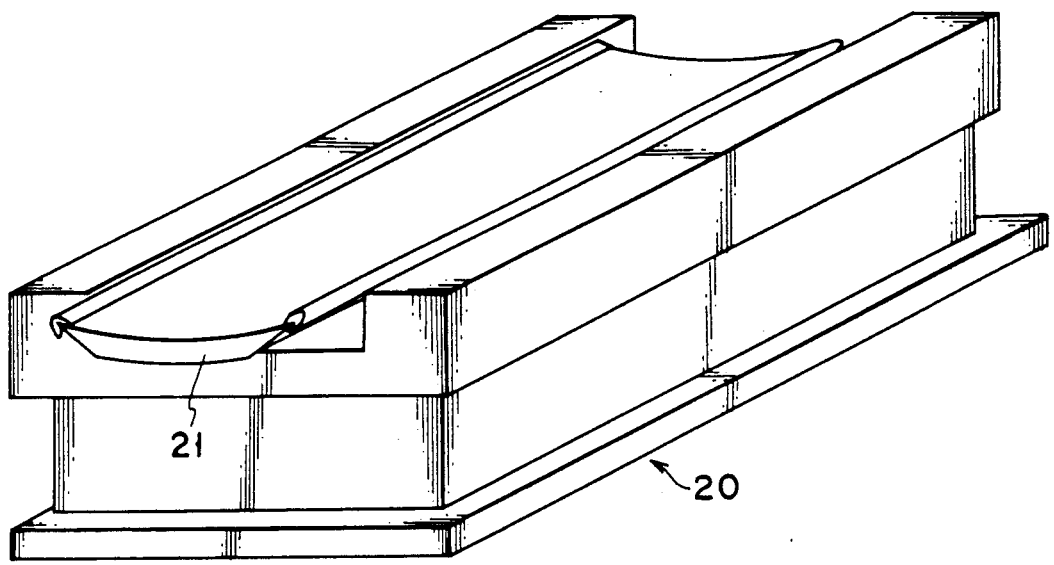
FIG. 2 is a perspective view of a bed unit attached to the x-ray CT apparatus shown in FIG. 1.

FIG. 2 shows bed unit 20 for the CT apparatus. Bed unit 20 is overlain by top table 21 which can move in the longitudinal direction of unit 20. Top table 21 is moved with the examined body thereon, and the examined body is inserted into a photographing opening of the gantry.

Figure 3:
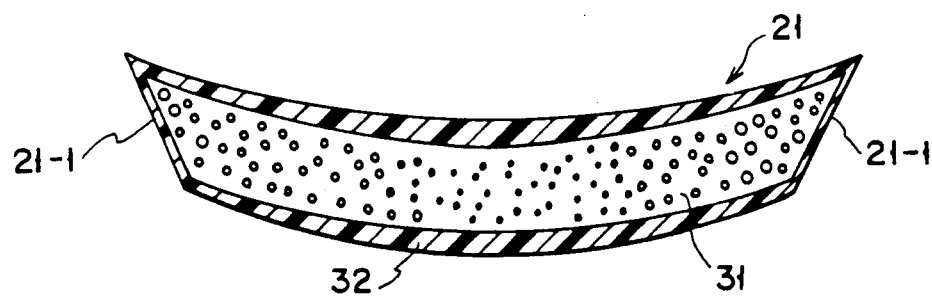
FIG. 3 is a sectional view of a top table mounted on the bed unit shown in FIG. 2.

In this embodiment, top table 21 is composed of core 31 made of plastic foam (e.g., acrylic resin) with a low x-ray absorption factor, and covering 32 made of a composite material (e.g., carbon fiber reinforced plastic or CFRP) with a low x-ray absorption factor and wrapping the core, as shown in FIG. 3. The foaming rate of the central portion of core 31 is lower than that of each longitudinally extending end portion of core 31, that is, the central portion is higher in density than the longitudinally extending end portions. By way of example, the foaming rate at the central portion is 5, and that at each end portion is 10. The foaming rate is defined as follows. If an object of 1 cm$^3$ increases its volume to 10 cm$^3$ after foaming, then the foaming rate is 10. The central portion of covering 32 is thick-walled, while its end portions are thin-walled.

With this arrangement, the x-ray absorption factor of each end portion 21-1 of top table 21 can be made lower than that of the central portion of the top plate, without lowering the strength or rigidity of the top table.

The following is a description of the function and effect of the present embodiment.

Figure 4:
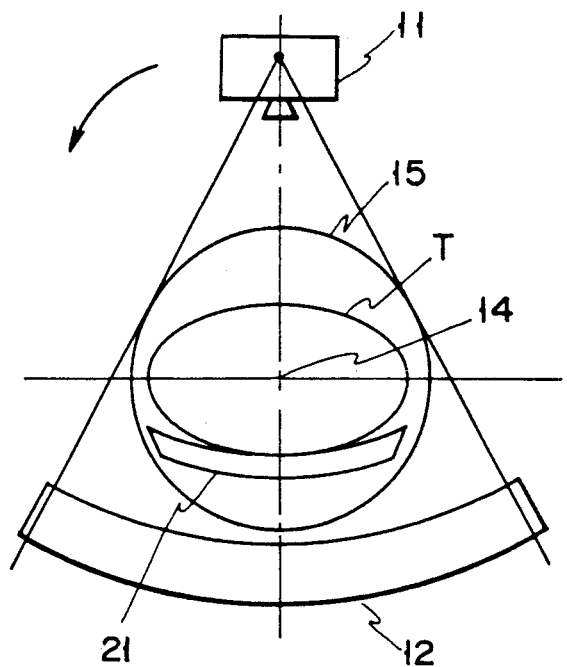
FIGS. 4 to 7 are schematic views of the x-ray CT apparatus for illustrating the operation thereof.

First, FIG. 4 shows a case in which x-ray tube 11 and detector 12 are shifted upward with respect to revolution center 14 so that effective field 15 is widest. In this case, patient T is an adult, whose trunk is to be radiographed. Since effective field 15 is so wide that whole top table 21, as well as the radiographed area of the patient's body, is situated within field 15. If the x-ray fan beams are revolved through 360° so that the projection data are detected, therefore, data on projection from all directions (360°) for all the area of top plate 21 can be obtained. Thus, there are no significant differences between the projection data, so that the resulting image is subject to no shading.

Figure 5:
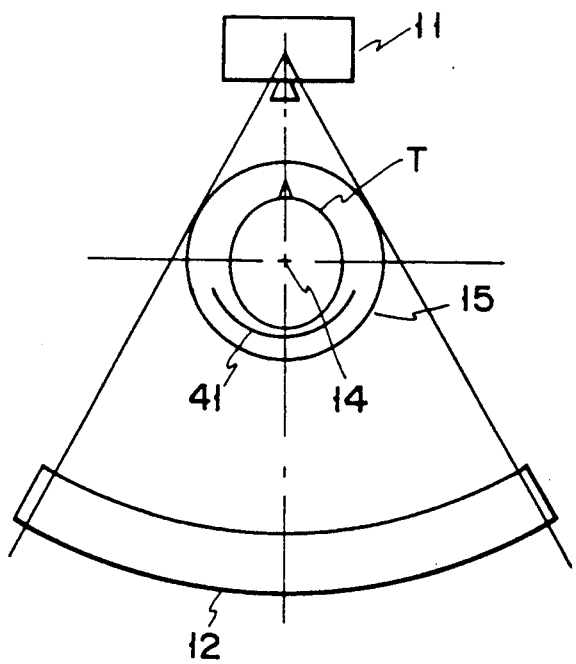

FIG. 5 shows a case in which x-ray tube 11 and detector 12 are shifted downward with respect to revolution center 14 so that effective field 15 is reduced. In the case of FIG. 5, the number of x-ray beams per unit length is larger than in the case of FIG. 4, so that the resolution of the image is higher. In this case, patient T is an adult, whose head is to be radiographed, and the effective field is relatively narrow. Since the patient's head and headrest 41 are situated in the effective field, however, there are no significant differences between the projection data, so that the resulting image is subject to no shading.

Figure 6:
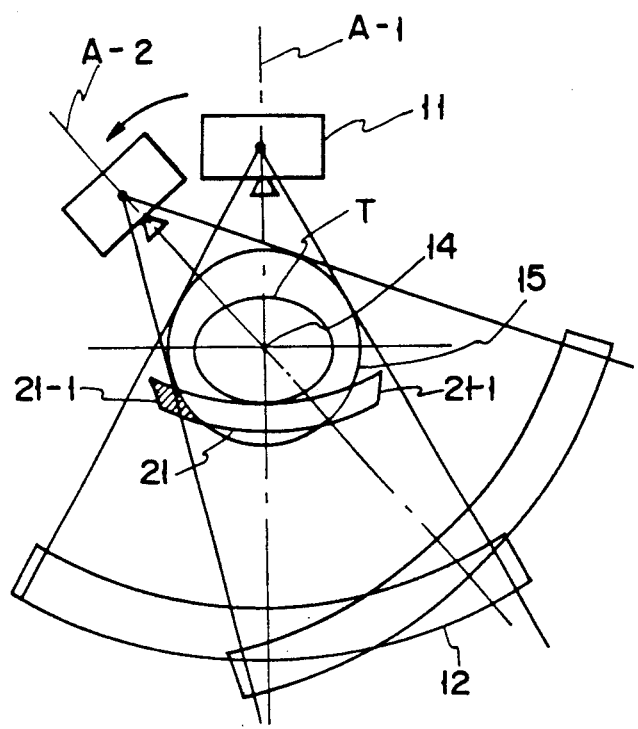

FIG. 6 shows a case in which patient T is an infant, whose trunk is to be radiographed. For safety's sake, the infant is laid on top plate 21 for adult. Also in this case, x-ray tube 11 and detector 12 are shifted with respect to revolution center 14 so that effective field 15 is reduced, in order to improve the resolution of the image.

In this case, however, both end portions 21-1 of top table 21 protrude from effective field 15 of scan. Thus, there have conventionally been the following problems. The smaller the effective field, or the greater the width of the top table, the higher the degree of protrusion of the end portions of the top table from the effective field is.

Thus, when x-ray tube 11 and detector 12 are located in position A-1 of FIG. 6, the fan beams emitted from tube 11 are detected by detector 12 after being transmitted through whole top table 21. Therefore, the projection data obtained include data on x-rays absorbed at end portions 21-1.

When x-ray tube 11 and detector 12 are located in position A-2 of FIG. 6, on the other hand, the fan beams emitted from tube 11 are detected by detector 12 without being transmitted through end portions 21-1 of top table 21. Therefore, the projection data obtained in this case do not include the data on the x-rays absorbed at end portions 21-1.

Figure 7:
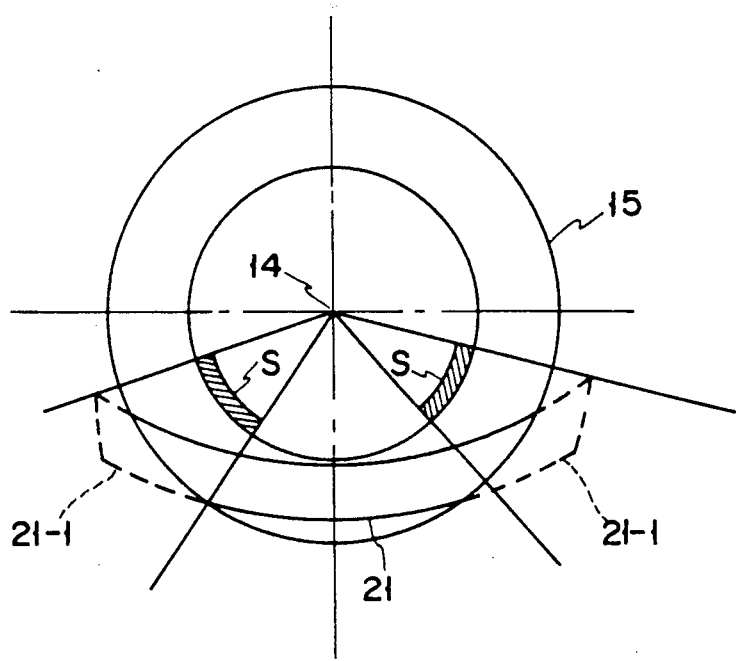

Thus, if end portions 21-1 of top plate 21 protrude from effective field 15, some fan beams are transmitted through end portions 21-1, and others are not. Accordingly, there are significant differences between the projection data. As a result, the reconstructed image is subject to shading. More specifically, the shading develops as high CTs at hatched portions S, as shown in FIG. 7 which illustrates the image on a display.

According to the present invention, in contrast with this, the x-ray absorption factor of end portions 21-1 of top table 21 is lower than that of the central portion of the top table. If end portions 21-1 of top table 21 protrude from effective field 15 of scan so that the fan beams are transmitted through portions 21-1, therefore, the beams can hardly be absorbed by portions 21-1. Accordingly, the projection data are hardly subject to any significant differences which depend on the transmission of the fan beams through end portions 21-1. Even though the image is reconstructed in accordance with the obtained projection data, therefore, it can be prevented from suffering shading. Thus, a high-quality reconstructed image can be obtained.

It is to be understood that the present invention is not limited to the embodiment described above. In the above embodiment, the x-ray absorption factor of end portions 21-1 of top table 21 is made lower than that of the central portion of the top table. Alternatively, however, the x-ray absorption factor of the end portions of the headrest may be made lower than that of the central portion of the headrest. Alternatively, moreover, a mat on the top plate may be formed in like manner.

Furthermore, a third-generation (RR-system) x-ray CT apparatus has been described in connection with the foregoing embodiment. However, the present invention is not limited to this arrangement, and may be also applied to a fourth-generation (SR-system) or fifth-generation (SS-system) CT apparatus. In the fourth-generation apparatus, number of detectors are arranged in a ring, and an x-ray tube is revolved. In the fifth-generation apparatus, a number of x-ray tubes and detectors are arranged in a ring.

Referring now to FIG. 1, the operation of the third-generation x-ray CT apparatus will be described.

A patient's body is located between x-ray source 11 and detector 12. X-ray source 11 and detector 12 are rotated clockwise facing each other.

Data acquisition unit 120 integrates x-ray transmission data by detection channels of detector 12 for every x-ray path. Unit 120 converts x-ray transmission data into a digital signal as digital projection data. The digital projection data is thus prepared for subsequent processing.

Image reconstruction unit 130 receives projection data on the patient's body, with respect to all directions, from data acquisition unit 120, and produces a tomographic image which reflects the degree of x-ray absorption at a position of the x-ray transmission direction of the patient, in accordance with, e.g., filter-correction back projection. Preprocessor 131 performs processing such as DC-component correction of the projection data and correction of a change in x-ray intensity. Convolver 132 convolutes the projection data, corrected by preprocessor 131, by using a blur recovery filter in units of projection directions, and thus performs centering. Back projector 133 back-projects the projection data in image memory 134 after convolution in each direction is performed by convolver 132. A tomographic image is stored in memory 134.

Image converter 140 converts an image in image memory 134 into a video signal which represents a density image. The video signal is supplied to display unit 150, whereupon the tomographic image is displayed on the display unit.

Control unit 160 comprises system controller 161 for controlling the operation of the whole system, console 162 through which an operator can enter instructions, x-ray controller 163 for controlling x-ray source 11 under the control of system controller 161, and scanner controller 164 for controlling the rotation of x-ray source 11 and detector 12.

Since x-ray source 11 and detector 12 are rotated in the x-ray CT apparatus, display unit 150 uses a circular screen to display the image thereon. The entire photographed area need not be displayed on the screen, and only a desired region thereof may be displayed on the screen. To attain this, the image may be enlarged or reduced so that the enlarged or reduced image is displayed on the screen. A large number of small squares, i.e., pixels, whose densities vary, are used to constitute a two-dimensional image.

Additional advantages and modifications will readily occur to those skilled in the art. Therefore, the invention in its broader aspects is not limited to the specific details, representative devices, shown and described herein. Accordingly, various modifications may by without departing from the spirit or scope of the general inventive concept as defined by the appended claims and their equivalents.

What is claimed is:

1. A patient support means for x-ray absorption compensation in computer tomography system, comprising:
    a patient support plate on which a patient will be laid and which includes a core member having two longitudinally extending end portions and a middle portion between the longitudinally extending end portions, both longitudinally extending end portions of the core member being lower in density than the middle portion thereof, the longitudinally extending end portions extending in a longitudinal direction of the patient and located at both sides of the patient in a width direction of the patient, whereby an x-ray absorption factor of each of the longitudinally extending end portions is lower than that of the middle portion.

2. A patient support means according to claim 1, wherein the core member is made of a foamed material, and
    a foaming rate of the longitudinally extending end portions is higher than that of the middle portion.

3. A patient support means according to claim 1, wherein the patient support plate further comprises a sheathe member covering the core member, and
    longitudinally extending end portions of the sheathe member corresponding to the longitudinally extending end portions of the core member are thinner than a middle portion of the sheathe member corresponding to the middle portion of the core member.

4. A patient support means according to claim 1, wherein the computer tomography system includes:
    means for radiating an x-ray in a fan shape to the patient laid on the patient support plate, so that the patient is scanned with the fan shaped radiating x-ray beam along one cross section of the patient;
    means for detecting the fan shaped radiating x-ray beam, preparing scanned x-ray transmission data in accordance with the detected x-ray beam, and constructing a tomographic image of the patient along the one cross section; and
    means for revolving the x-ray radiating means and the x-ray detecting means around the longitudinal axis or the patient laid on the patient support so that the x-ray beam radiation in the fan shape from the x-ray radiating means scans the patient on the patient support in a whole radial direction to the longitudinal axis.

5. A patient support means according to claim 4, wherein the computer tomography system further includes means for shifting the x-ray radiating means and the x-ray detecting means in the radial direction of the patient on the patient support with reference to the longitudinal axis.

* * * * *